(12) United States Patent
Forceville

(10) Patent No.: US 7,695,972 B2
(45) Date of Patent: Apr. 13, 2010

(54) METHODS AND KITS FOR THE IN VITRO DIAGNOSTIC OR FOR THE MONITORING OF A DISEASE INVOLVING AN INFLAMMATORY REACTION

(76) Inventor: Xavier Forceville, 12 Rue de la Champagne, Saint Germain sur Morin (FR) F-77860

(*) Notice: Subject to any disclaimer, the term of this patent is extended or adjusted under 35 U.S.C. 154(b) by 0 days.

(21) Appl. No.: 10/477,826

(22) PCT Filed: May 15, 2002

(86) PCT No.: PCT/EP02/05350

§ 371 (c)(1),
(2), (4) Date: Nov. 17, 2003

(87) PCT Pub. No.: WO02/093175

PCT Pub. Date: Nov. 21, 2002

(65) Prior Publication Data

US 2004/0126822 A1    Jul. 1, 2004

Related U.S. Application Data

(60) Provisional application No. 60/290,973, filed on May 16, 2001.

(51) Int. Cl.
*G01N 33/00* (2006.01)
*G01N 33/20* (2006.01)
*G01N 33/53* (2006.01)

(52) U.S. Cl. .......................... 436/74; 436/73; 436/801; 436/811; 435/7.1; 530/400

(58) Field of Classification Search .................. 435/4, 435/7.1, 7.4, 7.7, 7.9, 25–28, 189–192, 975; 436/86–87, 160, 811, 74, 801; 530/400
See application file for complete search history.

(56) References Cited

U.S. PATENT DOCUMENTS 6,303,295 B1 * 10/2001 Taylor et al. .................... 435/6
6,844,012 B1 * 1/2005 Forceville et al. ........... 424/702

FOREIGN PATENT DOCUMENTS

WO   WO 00/12101   *   3/2000
WO   WO 00/31131   *   6/2000

OTHER PUBLICATIONS

Strongin W. Sensitivity, specificity, and predictive value of diagnostic tests: definitions and clinical applications, found in Laboratory Diagnosis of Viral Infections, Edwin Lennette, 2nd Ed (1992).*
Mostert V, et al. A novel method for the purification of selenoprotein P from human plasma. Arch. Biochem. Biophys. 1998;2:326-330.*
Mostert V. Selenoprotein P: Properties, functions, and regulations. Arch. Biochem. Biophys. 2000;2:433-438.*
Hill KE, et al. Selenoprotein P concentration in plasma is an index of selenium status in selenium-deficient and seleniium-supplemented Chinese subjects. J. Nutr. 1996;126:138-145.*
Mostert, V. et al. Transforming growth factor-beta1 inhibits expression of selenoprotein P in cultured human liver cells. FEBS Letters. 1999;460:23-26.*
Persson-Moschos M et al.: "Selenoprotein P in Serum as a Biochemical Marker of Selenium Status" Analyst, London, GB, vol. 120, No. 3, Mar. 1995, pp. 833-836, XP002924559 p. 833, Radioimmunoassay of Selenoprotein P.
Nichol Colin et al: "Changes in the concentrations of plasma selenium and selenoproteins after minor elective surgery: Further evidence for a negative acute phase response?" Clinical Chemistry, vol. 44, No. 8 Part 1, Aug. 1998, pp. 1764-1766, XP001084140 ISSN: 0009-9147 p. 1764, right -hand column, lines 17-line 26: p. 1765, left-hand column, line 17-line table 1.
P. Galloway et al: "Effect of the inflammatory response of trace element and vitamin status" Ann. Clin. Biochem., 'Online! 2000, pp. 289-297, XP002206057 Retrieved from the Internet: <URL: www.leeds.ac.uk/acb/annals/annals_pdf/May00/ACB289.PDF>retrieved on Jul. 4, 2002! p. 291, right-hand column, paragraph 2.
Gartner R et al: "Significance of selenium in intensive care medicine. Clinical studies of patients with SIRS/sepsis syndrome!" Medizinnische Klinik (Munich, Germany: 1983) Germany Oct. 15, 1999, vol. 94 Suppl 3, Oct. 15, 1999, pp. 54-57, XP001088107 ISSN: 0723-5003 abstract.
Forceville X et al: "Selenium, systemic immune response syndrome, sepsis, and outcome in critically ill patients." Critical Care Medicine, United States Sep. 1998, vol. 26, No. 9, Sep. 1998, pp. 1536-1544, XP001088109 ISSN: 0090-3493 p. 1538, left-hand column p. 1538, right-hand column.

* cited by examiner

*Primary Examiner*—Unsu Jung
(74) *Attorney, Agent, or Firm*—Young & Thompson

(57) ABSTRACT

Method for the in vitro diagnostic or for the monitoring of a disease involving an inflammatory reaction within a patient, which comprises the steps of: a) providing a biological sample from the patient; b) measuring the amount of selenoprotein P which is contained in the biological sample; c) comparing the amount of selenoprotein P measured at step b) i) with the amount of selenoprotein P which is contained in a biological sample from an individual which is not affected with the disease; or ii) with the amount of selenoprotein P which was contained in a biological sample from the same patient.

5 Claims, No Drawings

METHODS AND KITS FOR THE IN VITRO DIAGNOSTIC OR FOR THE MONITORING OF A DISEASE INVOLVING AN INFLAMMATORY REACTION

FIELD OF THE INVENTION

The present invention relates to the field of the diagnostic and of the monitoring of several diseases involving an inflammatory reaction, especially those which are associated with damages to the vascular endothelium in human and animals.

BACKGROUND OF THE INVENTION

Severe sepsis and more particularly at a further stage, septic shock, leading to multiple organ failure are major medical problems in critically ill patients and are the most common cause of death in medical and surgical intensive care unit (ICU) (Definition and epidemiology This L G, Dhainaut J F; in Septic Shock, Dhainaut J F, This L G, G Parked; Sunders 2000). Septic shock is a public health problem because of its frequency (500 000 to 700 000 new cases per year in the United States), and of it mortality Fate (around 45%). The systemic repercussion of septic shock is considered as the result of an uncontrolled and generalized immuno-inflammatory reaction. In the case of septic shock, that reaction results from a systemic host response to invasive infection. (From Celsus to Galen to Bone: The Illnesses, Syndromes, and Diseases of Acute Inflammation, Marshall J C, Aarts M A, in Yearbook of Intensive Care and Emergency Medicine, Vincent J L ed.; Springer Verlag, 2001; 3-12). This reaction leads to organ dysfunction and, at a further stage, organ failure.

The physiopathology of septic shock could be considered as a consequence of an overproduction of free radicals (Novelli, G. P., Role of free radicals in septic shock, J Physiol Pharmacol; 1997,48 (4): 517-527) (Zimmerman, J. J., Defining the role of oxyradicals in the pathogenesis of sepsis, Critical Care Medicine; 1995, 23, (4): 616-617) This does not contradict the usual diagrams concerning septic shock but points to free radicals as being directly responsible for cellular damages. The main origin of this deleterious overproduction of free radicals would be the activated polynuclear neutrophils adhering to the venous postcapillary segment (Bast, A.; Haenen, G. R.; Doelman, C. J., Oxidants and antioxidants: state of the art, Am J Med; 1991, 91, (3C): $2S^{-13}S$). In septic shock, nitric oxide is known to have a marked role. It appears early in septic shock. Its deleterious effects on the organism seems to be essentially mediated by peroxynitrite (ONOO—), formed during the simultaneous synthesis of NO by endothelium cells and superoxide anion by phagocytic cells, such as polymorphonuclears. Moreover, the endothelium is a particular target for peroxynitrite, Selenium may be an efficient treatment of septic shock in particular for increasing selenoprotein P concentration (Selenium and the "free" electron"—Selenium a trace to be followed in septic or inflammatory ICU patients, Forceville X, Intensive Care Medicine; 2001, 27: 16-18).

The early diagnosis and treatment of septic shock have to be conducted in a state of emergency. In man, at the present time, in the only phase III positive therapeutical trial in the treatment of the inflammatory reaction of septic shock, patients had to begin treatment within the first 24 hours of septic shock (Efficacy and Safety of Recombinant Human Activated Protein C for Severe Sepsis, Bernard G. R., Vincent J L, Laterre P F, New England Journal of Medicine; 2001). In fact, microcirculation endothelium is rapidly damaged during septic shock. The massive alterations of endothelium have a major physiopathological role in the consequences of septic shock and lead to organ failure (Sepsis/septic shock: Participation of the microcirculation: An abbreviated review, Hinshaw L B Critical Care Medicine 1996, 24 (6), 1072-1078).

There is a need in the art to have a relatively simple and reproducible biological marker to precisely identify septic shock patients in order to have reproducible epidemiological data, to define appropriate populations of patients to be included in sepsis trials, to identify populations of patients who might benefit from those therapies, and to monitor the evolution of septic shock under those therapies. Moreover that marker should ideally target the biological process or a biological process responsible for the manifestation of septic shock. "The search for such (a) marker(s) is an important priority for ongoing investigations" (From Celsus to Galen to Bone: The Illnesses, Syndromes, and Diseases of Acute Inflammation, Marshall J C, Aarts M A, in Yearbook of Intensive Care and Emergency Medicine, Vincent J L ed.; Springer Verlag, 2001; 3-12).

However, the diagnostic of sepsis and septic shock remains presently complex and depends on definitions that are based on clinical manifestations (Groeneveld, This, in Dhainaut 2000, Pg. 355). They characterize a subgroup of patients with systemic inflammatory response syndrome not only due to infection but also to diseases such as pancreatitis, extended burns, and polytrauma. For further details, see the American College of Chest Physicians and the Society of Critical Care Medicine, conference consensus, Chicago 1991 (The ACCP-SCCM consensus conference on sepsis and organ failure, Chest 1992; 101:1644-55), and the article by Marshall and Aarts (From Celsus to Galen to Bone: The Illnesses, Syndromes, and Diseases of Acute Inflammation, Marshall J C, Aarts M A in Yearbook of Intensive Care and Emergency Medicine, Vincent J L ed.; Springer Verlag, 2001; 3-12). Sepsis, severe sepsis and at a further stage septic shock may be due to infection associated or not with detected bacteremia due to bacteria, but also fungi or virus.

Septic shock is defined as a sepsis-induced hypoperfusion (i.e. systolic blood pressure <90 mmHg or a reduction of $\geq 40$ mmHg from baseline) despite adequate fluid resuscitation along with the presence of perfusion abnormality that may include but are not limited to lactic acidosis, oliguria or an acute alteration in mental state. Patients who are receiving inotropic or vasopressor agents may not be hypotensive at the time that perfusion abnormalities are measured (Bone, 1992, ref. 2925) (Definition and epidemiology This L G, Dhainaut J F; in Septic Shock, Dhainaut J F, This L G, G Park ed.; Sunders 2000). This clinical definition established in the ACCP-SCCM consensus conference on sepsis and organ failure, Chicago, August 1991 remains the only valid one (The ACCP-SCCM consensus conference on sepsis and organ failure, Chest 1992; 101:1644-55).

Different markers of septic shock, and especially of its initial manifestation, have been proposed, but are non-specific and insensitive (Diagnosis: from clinical signs to haemodynamic evaluation, Groeneveld A B J, This G T; in Septic Shock, Dhainaut J F, This L G, G Park ed.; Sunders 2000). As activation of inflammatory pathways, including the cytokine network, is considered to play a major role in the pathogenesis of septic shock, cytokines have been extensively studied as a potential marker of septic shock (Cytokines and Anticytokines in the Pathogenesis of sepsis, van der Poll T, van Deventer S J H, Infectious disease Clinics of North America; 13 (2) 1999; 413-426). In comparison with other cytokines, IL-6 (a mixed pro- and anti-inflammatory cytokine) has been reported most consistently in the circulation of septic patients. However, IL-6 level shows considerable variation, and it is not possible to define a cut-off value to identify septic shock patients (Cytokines and Anticytokines in the Pathogenesis of sepsis, van der Poll T, van Deventer S JH, Infectious disease Clinics of North America; 13 (2) 1999; 413-426) Procalcitonin (PCT), C-reactive protein (CRP), leukocytosis, lactate concentration, coagulation parameters, and other parameters have also been proposed to identify septic shock patients (Diagnosis of sepsis: Novel and Conventional Parameters, Rheinhart K, Meisner M and Hartog C, Advances in sepsis, 2001; 42-51). However, though they seem to be useful parameters to improve the diagnosis and monitoring of septic shock, they cannot clearly identify septic shock patients due to their lack of specificity and the diagnosis of septic shock remains based on clinical parameters. (From Celsus to Galen to Bone: The Illnesses, Syndromes, and Diseases of Acute Inflammation, Marshall J C, Aarts M A, in Yearbook of Intensive Care and Emergency Medicine, Vincent J L ed.; Springer Verlag, 2001; 3-12). Presently, laboratory abnormalities can only be supportive for the diagnosis of sepsis and cannot prove the presence of septic shock. Taken together, abnormalities in hematological and chemical laboratory parameters may only constitute indicators of septic shock (Diagnosis: from clinical signs to haemodynamic evaluation, Groeneveld A B J, This G T; in Septic Shock, Dhainaut J F, This L G, G Park ed.; Sunders 2000). Each alone of this parameters carries little meaning. (Defining a Clinical Syndrome of Systemic inflammation, Vincent J L, Byl B, Sepsis, 200; 4:15-19).

Their is also an urgent need in the art to find a specific and reliable parameter to define septic shock patients. A precise definition of septic shock patients could allow an early diagnosis and a follow-up of septic shock. This parameter should ideally be closely related to the physiopathological process of septic shock (From Celsus to Galen to Bone: The Illnesses, Syndromes, and Diseases of Acute Inflammation, Marshall J C, Aarts M A, in Yearbook of Intensive Care and Emergency Medicine, Vincent J L ed.; Springer Verlag, 2001; 3-12).

SUMMARY OF THE INVENTION

The present invention is based on the observation that selenoprotein P can be used as a biochemical marker of septic shock, both in man and in animals, and more generally as a biochemical marker of the severity of the systemic inflammation response syndrome (SIRS).

Thus, a first object of the present invention consists of a method for the in vitro diagnostic or for the monitoring of a disease involving an inflammatory reaction within a patient, wherein said method comprises the steps of:
  a) providing a biological sample from said patient;
  b) measuring the amount of selenoprotein P Which is contained in said biological sample;
  c) comparing the amount of selenoprotein P measured at step b)
    i) with the amount of selenoprotein P which is contained in a biological sample from an individual which is not affected with the disease; or
    ii) with the amount of selenoprotein P which was contained in a biological sample from the same patient.

By "a disease involving an inflammatory reaction", it is intended herein a disease wherein the inflammatory reaction is associated with an activation of the peripheral blood phagocytic cells, namely monocytes/macrophages and most importantly polymorphonuclear cells and more specifically neutrophils. More preferably, a "disease involving an inflammatory reaction" as defined above is also associated with a damage to the vascular endothelial cells.

By "amount" of selenoprotein P, it is intended herein any parameter or unit of measure which allows the quantification of selenoprotein P in a sample. An amount of selenoprotein P may be expressed as an absolute quantity in a sample (e.g. number of moles of selenoprotein. P) or as a concentration (e.g. nmol/L of selenoprotein P in the sample).

The damage to the vascular endothelial cells may be present at the onset of the disease or alternatively is a consequence of the onset of the disease and thus consists of a secondary damage to the vascular endothelial cells.

In a first preferred embodiment, the disease consists of a systemic inflammation response syndrome (SIRS), and most preferably of a septic shock.

In a second preferred embodiment, the disease consists of a chronic inflammatory disease. Said chronic inflammatory disease may be selected from the group consisting of a systemic disease such as polyarteritis nodosa. The chronic inflammatory disease may also be a disease related to a bacterial, a fungal or a viral infection or may be an eclempsia, therefore the follow up od selenoprotein P during pregnacy may be done during routine pregnancy follow up.

In a further preferred embodiment, the occurrence or the aggravation of the disease is diagnosed in a further step d) when the amount of Selenoprotein P measured in the biological sample is lower than the normal amount which is contained within non-affected individuals or when the amount of selenoprotein P measured in the biological sample is lower than that measured in a sample from the same patient in a former test.

In another preferred embodiment, the persistence of the disease is diagnosed in a further step d) when the amount of Selenoprotein P measured in the biological sample is lower than the normal amount which is contained within non-affected individuals or when the amount of selenoprotein P measured in the biological sample is lower than or not higher than, or equal to, the amount measured in a sample from the same patient in a former test.

In a still further preferred embodiment of the method disclosed above, the recovering from the disease is diagnosed in a further step d) when the amount of selenoprotein P measured in the biological sample is at least equal to the normal amount which is contained within non-affected individuals or when the amount of selenoprotein P measured in the biological sample is higher to that measured in a sample from the same patient in a former test.

In a further preferred embodiment of the method above, mortality is predicted when the amount of selenoprotein P which is measured within a serial of biological samples collected during the time period of the therapeutical treatment is always lower than 20 nmo/L, preferably lower than 10 nmol/L.

The invention also relates to a kit for the in vitro diagnostic or for the monitoring of a disease involving an inflammatory reaction associated with a damage of the vascular endothelial cells within a patient, wherein said kit comprises (i) means for assaying the amount of Selenoprotein P contained in a biological sample.

In a first preferred embodiment, the kit of the invention further comprises (ii) a sample or a plurality of samples containing each respectively a predetermined amount of Selenoprotein P to be used as a standard reference.

In a second preferred embodiment of the kit according to the invention, the means for assaying the amount of Selenoprotein P contained in the biological sample consist of antibodies directed against Selenoprotein P.

DETAILED DESCRIPTION OF THE INVENTION

It has now been found according to the invention that a marked decrease in the blood concentration of selenoprotein P is measured in patients suffering from diseases that involve an inflammatory reaction.

The inventor has now shown that a marked decrease in the blood concentration of selenoprotein P occur in patients affected with severe sepsis, particularly in patients which are affected with a systemic inflammation response syndrome (SIRS) and that a more further decrease in the blood selenoprotein P level is measured in patients which are undergoing a septic shock.

Selenoprotein P has been known since 1971. It is the only selenoprotein to contain more than one selenium atom per polypeptide chain in the form of 10 selenocysteine residues per polypeptide (Orphan selenoproteins Burk R F, Hill K E BioEssays 21 (3): 231-237, 1999) (Selenoprotein P: Properties, Functions, and Regulation Mostert V, Archives of Biochemistry and Biophysics; 376 (2): 433-438, 2000). Selenoproteins are defined as proteins containing selenocysteine. Selenocysteine is known to be the 21st amino acid by the replacement of sulfur to selenium in the cysteine. The comparison of deduced amino acid sequences of selenoprotein P from different species indicates almost complete conservation of cysteine and selenocysteine residues when these amino acids are considered together. Selenoprotein P is mainly synthesized in the liver. There are at least two distinct isoforms of selenoprotein P in human plasma (A Novel Method for the Purification of Selenoprotein P from Human Plasma, Mostert V, Lombeck I, Abel J, Archives of Biochemistry and Biophysics; 357 (2): 326-330, 1998).

Selenoprotein P is present in a large amounts of the surface of the endothelial cells. Through its heparin-binding properties it could bind to the inflammated endothelium (Burk, R. F.; Hill, K. E.; Boeglin, M. E.; Ebner, F. F.; Chittum, H. S., Selenoprotein P associates with endothelial cells in rat tissues, Histochem Cell Biol; 1997, 108 (1), 11-15).

Because of the high stability of the selenoprotein P plasma concentration in healthy individuals as well as in individuals affected with diverse pathologies which are not involving an inflammatory reaction, selenoprotein P consists of a highly reliable marker both for diagnosing inflammatory diseases and for monitoring the recovering of patients from these inflammatory diseases, for example during the whole time period of treatment and even after the end of the treatment in order to ensure the total recovery of the patient from the disease.

In anorexic, malnutrition, selenium deficiency, in particular in some countries of China, severe alcoholic disease i.e. cirrhosis, dialyzed or apheresis patients as in inflammatory bowel diseases patients, seleno protein P plasma concentration may be expected to be low, reflecting the low selenium status of these patients and perhaps in case of inflammatory diseases the chronic consumption and/or reduced synthesis for severe liver diseases i.e. cirrohosis.

Thus, the present invention firstly relates to a method for the in vitro diagnostic or for the monitoring of a disease involving an inflammatory reaction within a patient, wherein said method comprises the steps of:

a) providing a biological sample from said patient;

b) measuring the amount of selenoprotein P which is contained in said biological sample;

c) comparing the amount of selenoprotein P measured at step b)

i) with the amount of selenoprotein P which is contained in a biological sample from an individual which is not affected with the disease; or ii) with the amount of selenoprotein P which was contained in a biological sample from the same patient.

By a "biological sample", it is herein intended a blood sample, such as a whole blood sample. Most preferably, the biological sample consists of a blood plasma sample.

According to a first aspect of the method, the disease involving an inflammatory reaction involving an inflammatory reaction consists of a Systemic Inflammation Response Syndrome (SIRS).

According to a second aspect, the disease involving an inflammatory reaction consists of a septic shock.

According to a third aspect, the disease involving an inflammatory reaction associated with a damage of the vascular endothelial cells consists of a chronic inflammatory disease.

According to a fourth aspect, the chronic inflammatory disease is selected form the group consisting of the inflammatory bowel disease or a systemic disease such as polyarteritis nodosa.

In a fifth aspect, the disease involving an inflammatory reaction consists of a chronic inflammatory disease related to a bacterial, a fungal or a viral infection. The diagnostic or the monitoring of the evolution of the inflammatory reactions occurring during a HIV infections is an illustrative example of the use of the diagnostic method disclosed herein.

Most preferably, the method according to the invention is highly useful for diagnosing as well as monitoring septic shock disorders which require a treatment based on a high level of catecholamines such as norepinephrine and epinephrine.

More preferably, the mthod according to the invention is performed for the diagnosis, the monitoring or for pronostic purposes for the following pathologies involving inflammatory reactions:

a/ Main target diseases (for diagnostic, severity, pronostic)
⇒Septic shock associated or not with bacteremia, funguemia, parasitemia, viremia, associated or not with multiple organ failure, b/ Associated target diseases (for pronostic and severity, also for diagnostic)—SIRS:

infections without septic shock ie. with severe sepsis, (Ie. peritonitis, pneumonia, meningitidis, catheter related infection, urinay, biliary tract infection, atack of malaria, especially cerebral malaria) non infectious origin:pancreatitis, burns, polytrauma associated of not with fat embolism, massive transfusion, adult respiratory distress syndrom (ARDS), or similar diseases especially in newborn acute renal failure (ARF) related to inflammatory disease, major surgery.

shock whatever the origin especially with multiple organ dysfunction and severe hypoperfusion: i.e. hemorragic, cardiogenic, anaphylactic ischemia-reperfusion:

crush syndrom, aortic cross clamping, ischemia with reperfusion (ie. mesenteric, lower limb ischemia).

prolonged status epilepticus, acute rhabdomyolisis (ie. exertionnal rabdomyolisis) malignant hyperthermia.

eclampsia severe status asthmaticus tumoral lysis syndrom, exacerbation of systemic diseases. (Acute) hemolytic syndrom Metals intoxication i.e. iron (Fe), copper (Cu); all intoxication or poisonning involving vascular oxidative stress (i.e. paraquat, diquat) transplantation (especially if associated with graft reaction, second set, graft versus host reaction).

c/ All diseases involving oxidative vascular damages, for the folow-up especially in cases of exacerbation and the monitoring of treatment involving or not selenium compound.

⇒Chronic infection:
  i.e. HIV, endocarditis, (infection related arteritis i.e. syphilis)
⇒Systemic diseases: (especially those associated with elevated ANCA):
⇒i.e necrotizing angeitis, Wegner's syndrome, polyarteritis nodosa, allergic granulomatosis, temporal arteritis, nephroangiosclerosis, Takayasus's disease, Buerger's disease
  Autoimmune diseases: i.e. rheumatoid arthritis, systemic lupus erythematosus (LES), acute rheumatic fever, dennatomyositis, systemic scleroderma thrombotic thrombocytopenic purpura
⇒hematologic and cancerologic diseases-associated with elevated cytokines (i.e. TNF-α) or tumoral lysis, or endothelium aggression
  Kahler's disease, Lymphoma especially T cell Lymphoma,
  tumoral lysis syndrom either spontaneous or induced by anti carcinologic treatment in hematologic or tumoral diseases (i.e. acute leukemia, solid tumor especially with elevated cytokines).
  Immun complex diseases (i.e. Berger's disease)
⇒Atherosclerosis (especially for folow-up and the monitoring of treatment prevention or for acute exacerbation, including or not selenium)
  Post-operative vascular restenosis folowing vascular angioplasty Diabetes (diabetic angiitis)
⇒Pregancy follow-up, monitoring of treatment (especially for the early detection of preeclampsia).
⇒Severe liver diseases, inflammatory bower disease.

In general, the method of the invention enables the one skilled in the art to diagnostic and monitor patients with the inflammatory diseases selected from the group of inflammatory diseases which are defined in the ACCD-ISCM Conference consensus (from Celsus to Galen to Bone: The illnesses syndromes and diseases of acute inflammation, Marshall J C, Aarts M A, in Yearbook of Intensive Care and Emergency Medicinee, Vincent J L ed.; Springer Verlag, 2001; 3-12).

In the general population, selenoprotein P plasma concentration is stable, though it could be somewhat affected by the selenium nutritional status of the population. In a survey of 414 people from various European countries, selenoprotein P level varies from 100% for Spain, to 76% for Greece (Variation in selenoprotein P concentration in serum from different European regions, Marchaluk E, Persson-Moschos M, Thorling E B, Akesson B, Eur J Clin Nutr, 1995; 49 (1): 42-48). Selenoprotein P appears to be an index of selenium nutritional status especially in the case of low selenium nutritional status. Indeed, in the Finland studies, a baseline selenium intake of about 100 μg/day abolishes the increase of selenoprotein P under oral supplements of 200 μg/day selenium, contrary to what was observed in the case of a baseline selenium intake of about 40 μg/day (Plasma selenoprotein P levels of healthy males in different selenium status after oral supplementation with different form of selenium, Perssonn-Moschos M, Alftan G, Akesson B, Eur J Clin Nutr; 1998, 52 (5): 363-367). Also, In the United States selenium nutritional status is known to be higher than in Europe (Rayman, M. P., The importance of selenium to human health, Lancet; 2000, 356: 233-41). Compared to other selenoprotein, such as glutathion peroxidase, selenoprotein P concentration is better preserved during the decrease of selenium intake (Selenoprotein P in serum as a biochemical marker of selenium status, Perssonn-Moschos M, Huang W, Srikumar T S, Akesson B, Lindeberg S, Analyst, 1995; 120 (3): 833-836).

As it is detailed hereabove, although the selenoprotein P plasma concentration is highly stable, some differences in the normal selenoprotein P plasma concentration were observed when individuals from various geographical origins were compared (see Marchaluk et al., 1995, Perssonn-Moschos et al., 1998; Rayman et al., 2000; OP. Cit.).

The discrepancies in selenoprotein P concentration which are observed in individuals belonging to distinct countries of origin do not require an adaptation of the method described above depending of the country of birth or of the genealogy of the patient tested, since these discrepancies do not significantly affect the statistical significance of the marked decrease in the selenoprotein P concentration, except in countries with very low selenium intake i.e. part of China, Finland without supplementation, New Zealand.

Nevertheless, in a most preferred embodiment of the method described herein, the amount of selenoprotein P which is measured at step b) is compared, at step c), with the amount of selenoprotein P which would be expected within a group of non-affected individuals from the same geographical origin than that of patient tested.

Consequently, when the patient originates from Europe, United States of America, Australia, or an asian country, the amount of selenoprotein P which is measured at step b) will be preferably compared, at step c) of the method, with the mean amount of selenoprotein P which is contained in the same biological sample of a group of non-infected individuals originating respectively from Europe, United States of America, Australia or an asian country.

In a further most preferred embodiment of the method, the country of origin may be taken into account, such as France, Spain or Greece, for example.

In a specific embodiment of the invention, the method described above allows the diagnosis of the occurrence of the disease in a further step d), when the amount of selenoprotein P which is measured in the biological sample of the patient tested is statistically lower than the normal amount which is contained within non-affected individuals.

In a further particular embodiment of the invention, the method described above allows to diagnose the persistence of the disease in a further step d), when the amount of selenoprotein P which is measured in the biological sample of the patient tested is lower than the normal amount which is contained within non-affected individuals, or alternatively when the amount of selenoprotein P is lower or not significantly higher than the amount found for the same patient in a former test.

In still a further embodiment of the invention, the method allows the diagnosis of the recovering of the patient from the disease in a further step d), when the amount of selenoprotein P which is measured in the biological sample of the patient tested is at least equal to the normal amount which is contained within the non-affected individuals, or alternatively when the amount of selenoprotein P is higher than the amount found for the same patient in a former test.

By <<at least identical>> as used herein, is intended an amount of selenoprotein P which is of a value which is at least not statistically distinct from the mean amount of selenoprotein P which is contained in the biological sample which is compared.

Without wishing to be bound by any particular theory, the inventor believes that the treatment of patients affected with a disease involving an inflammatory reaction associated with a damage to the vascular endothelial cells, particularly patients affected from SIRS or a septic shock, may need to obtain selenoprotein P plasma concentration values which are higher than those found in non-affected individuals. This situation may be the consequence of the therapeutical treatment based mainly on the administration of selenium. A supra-normal value of selenoprotein P plasma concentration may indicate a patient status wherein the endothelium is protected against endothelium oxydative aggression, whether it be acute or chronic.

Thus, in another particular embodiment of the invention, the method disclosed herein allows to diagnose the recovering from the disease in a further d), when the amount of selenoprotein P which is measured in the biological sample of the patient tested is higher than the normal amount which is contained within the non-affected individuals.

Preferably, the standard level of selenoprotein P plasma concentration which is contained in a biological sample from an individual which is not affected with the disease involving an inflammatory reaction associated with a damage to the vascular endothelial cells, at step c) of the method, is of at least 50 nmol/L. Most preferably, this selenoprotein P plasma concentration value is comprised between 40 and 80 nmol/L, advantageously between 40 and 70 nmol/L and most preferably between 40 and 60 nmol/L.

Most preferably, the selenoprotein P plasma concentration is indicative of a disease involving an inflammatory reaction associated with a damage to the vascular endothelial cells when the amount of selenoprotein P which is measured within the biological sample of the patient tested is lower than 30 nmol/L.

In a particular embodiment, the diagnostic of a selenoprotein P plasma concentration of less than 20 nmol/L is indicative of patients with sceptic shock requiring high level of catecholamines such as norepinephrine and epinephrine.

In a further embodiment, the diagnostic of a selenoprotein P plasma concentration of less than 15 nmpol/l and most-preferably of less than 10 nmol/l is predictive of mortality, especially when there is a persistence of a weak selenoprotein P amount during a selenium-based treatment of the patient.

However, at the stage of patients recovering from the disease, the inventor has observed supranormal values of selenoprotein P plasma concentration up to 106 nmol/L in recovering septic shock patients who survived, and supra normal values up to 181 nmol/L in non SIRS aggressed patients.

In a still further embodiment, the methods of the invention allows to predict mortality when the amount of selenoprotein P which is measured within a serial of biological samples collected during the time period of the therapeutical treatment is always lower than 20 nmo/L, preferably lower than 10 nmol/L.

Without wishing to be found by any particular theory, the inventor believes that the increase of selenoprotein P may be an interesting defense mechanism of the endothelium in situation of aggression. This reinforces the interest of the monitoring of selenoprotein P plasma concentration in all situations of generalized blood inflammation associated with immediate or secondary endothelium oxydative damages, whether or not it is associated with a selenium-based treatment or supplementation.

According to a specific embodiment of the method disclosed herein, the comparison step c) might take into account previously known chronic deficiencies in selenoprotein P of the tested patient, in order to avoid interpreting a weak decrease of selenoprotein P plasma concentration as regards the selenoprotein P standard concentration as indicative of an inflammatory disease.

As it is disclosed herein, the method of the invention allows the use of a novel biochemical marker, namely plasma concentration of selenoprotein P, in order to diagnose septic shock, and even the severity of the septic shock in man and in animal.

Moreover, the follow up of the selenoprotein P plasma concentration in a patient permits the monitoring of the evolution of the disease, for example septic shock. A persistent low level of selenoprotein P plasma concentration less than 20 nmol/L or 30 nmoL, especially if abundant selenium administration is provided during the therapeutical treatment, will correspond to the persistence of the systemic inflammation which was diagnosed according to the method of the invention.

Indeed, the method of the invention, by following up the plasma concentration of selenoprotein P, is very useful to monitor the benefit to the patient of a selenium-based treatment. Further, the persistence of a low level of selenoprotein P consists of a marker of the gravity and the mortality of the disease in a septic shock patients.

In a most preferred embodiment, the measure of the amount of selenoprotein P which is, contained in the biological sample of the patient tested, in step b) of the disclosed method, consists of an immuno assay wherein antibodies directed against selenoprotein P are used.

For performing such an immunoassay, the one skilled in the art will advantageously refers to the article of Mostert et al. (1998, Archives of Biochemistry and Biophysics, volo. 357 (2): 326-330).

When performing the method of the invention for monitoring purposes, said method will be performed at least daily during the period of time starting from the admission of the patients in an emergency care unit of an hospital. After this critical period, the method of the invention may be performed every two-days time period during the therapeutical treatment in order to monitor the recovering of the patients from the disease.

A daily dosage of selenoprotein P is preferred for acute diseases, especially if selenium-based treatment—e.g. by selenoprotein P—in order to achieve the optimal selenoprotein P plasma concentration adapted to the disease and its severity. Then, a dosage every two days periods or a weekly dosage is advantageous during the recovering period and then monthly after recovering of the normal selenoprotein P plasma concentration.

For chronic diseases in the absence of an acute disorder, or in cases of pregnancy, selenoprotein P dosages may be part of the routine biological examination.

Monitoring of selenium-based treatment can be achieved with selenoprotein P plasma concentration monitoring in order to obtain optimal selenoprotein P concentration according to the gravity of the disease and the importance of oxidative stress in the blood compartment.

In cases of septic shock with high level of oxidative stress in the blood compartment, it could be appropriate to obtain and maintain very high level of selenoprotein P much higher than the reference values.

Another object of the present invention consists of a kit for the in vitro diagnostic or for the monitoring of a disease involving an inflammatory reaction within a patient wherein said kit comprises (i) means for assaying the amount of selenoprotein P contained in a biological sample.

In a preferred embodiment, said kit further comprises (ii) a sample or a plurality of samples containing each respectively a predetermined amount of: selenoprotein P to be used as a standard reference.

Most preferably, said kit comprises one standard sample containing selenoprotein P at a determined concentration said concentration being comprised between 50 and 80 nmol/L, and most preferably about 50 nmol/L selenoprotein P.

In the embodiment wherein said kit comprises a plurality of standard samples containing selenoprotein P, the respective concentration are preferably 200, 100, 50, 30, 20 and 10 nmol/L selenoprotein P which are used to generate a standard curve allowing a precised determination of the selenoprotein P plasma concentration within the biological sample of the patient tested.

In a most preferred embodiment, the standard samples contain a selenoprotein P in a liquid solution, either a physiological saline buffer (e.g. minimum essential medium—MEM) or a plasma sample containing a predetermined concentration of selenoprotein P.

Standard samples of selenoprotein P may be contained in lyophilized form in a vial that will be added with the required volume of a suitable buffer at the time of use of the kit.

In a specific embodiment of the kit above, the means for assaying the amount of selenoprotein P contained in the biological sample consist of antibodies directed against selenoprotein P. Most preferably, said antibodies are those disclosed by MOSTERT et al. (1998).

Thus, the kit of the invention may also contain a vial containing the antibodies directed against selenoprotein P, either in suspension in a suitable buffer or alternatively under a lyophilized form.

By the determination of selenoprotein P plasma concentration by immunoblot analysis using purified selenoprotein P as a standard (A Novel Method for the Purification of selenoprotein P from Human Plasma, Mostert V, Lombeck I, Abel J, Archives of Biochemistry and Biophysics; 357 (2): 326-330, 1998), the reference level of selenoprotein P in the general population is about 50 nmol/L and more than 40 nmol/L. Selenoprotein P plasma concentration could be considered as low when it is less than 30 nmol/L and very low when it is less than 10 nmol/L.

The present invention will be further disclosed by, without in any case being limited to, the following examples.

EXAMPLES

In a preliminary study on 21 ICU patient and 7 healthy volunteers, selenoprotein P plasma concentration has been measured by immunoblot analysis using purified selenoprotein P as a standard (A Novel Method for the Purification of selenoprotein P from Human Plasma, Mostert V, Lombeck I, Abel J, Archives of Biochemistry and Biophysics; 357 (2): 326-330, 1998). In this study, 7 septic shock patients were included among the 21 ICU patients. Dosages have been realized at admission in ICU and later on at weekly intervals during their ICU length of stay. At admission, a very low selenoprotein P plasma concentration was observed in septic shock ICU patients (see Table 1 below) compared to non systemic inflammatory ICU patients. Extremely low level of selenoprotein P plasma concentration, even undetectable, was observed only in septic shock patients during their length of stay. Decrease of selenoprotein P was associated with severe inflammatory adverse events such as severe infections or acute respiratory distress syndrome. Last measurement before death was very low in the 3 septic shock patients who died compared to the value of the 3 defined as non severe SIRS patients who died. These selenoprotein P value was significantly lower than the one observed in the 3 patients who died in the non inflammatory group (p<0.05; Mann-Whitney test). It is to underline that this difference is significative despite the small number of patients involved.

The level of selenoprotein P at admission was poorly correlated (r about 0.3) with gravity index as measured to the Simplified Acute Physiology Score II (SAPS II) (A new simplified acute physiology score (SAPS II) based on European/North American multicenter study, Le Gall J R, Lemeshow S, Saulnier F, JAMA 1993; 270: 2957-2963).

This indicates that selenoprotein P doesn't assess the global gravity of the patients, but rather measures septic shock's (and SIRS's) gravity.

TABLE 1

Selenoprotein P plasma concentration at admission in septic shock ICU patients

|  | septic shock patients (all intubated) | Including septic shock patients with grade 4 in the cardiovascular function scale of the SOFA score |
|---|---|---|
| number of patients | (7 patients) (measurement at admission on only 6 patients) | (4 patients) (measurement at admission on only 3 patients) |
| Selenoprotein P | 15 ± 11 nmol/L (1-28) | 16 ± 9 nmol/L (7-28) |
| Mortality | (3 patients) | (3 patients) |

SOFA (The SOFA (Sepsis-related Organ Failure Assessment) score to describe organ dysfunction/failure, Vincent JL, Moreno R, Takala J and al, Intensive care Medicine 1996, 22: 707-710).
Results are given in mean ± standard deviation; followed by minima and maxima in brackets.

Example 2

Selenoprotein P Measurement in Septic Shock Patients and Comparison with Healthy-Volunteers and with Other ICU Patients.

The selenoprotein P plasma concentration at admission was significantly lower in the septic shock patient group compared to the non severe SIRS (see below for definition, and Table 2) patient group (p=0,0015; Mann-Whitney test), and healthy volunteers (p=0.003). It is to underline that this difference is significative despite the small number of patients involved, supporting the marked difference between the two groups.

As well, The selenoprotein P plasma concentration at admission was significantly lower in the severe SIRS patient group compared to the non severe SIRS (p<0.05) and to the healthy volunteer group (p<0.01) (see below Table 2).

Non severe SIRS patients were defined as patients without suspected or proven severe infection or septic shock, severe acute pancreatitis, extended burns; without post operative event with a SAPS II of more than 30; and without exposition to major ischemia-reperfusion process such as aortic cross clamping, inferior leg ischemia-reperfusion, mesenteric vascular ischemia.

Mean gravity index score, as defined by the SAPS II value, was lower in the non SIRS patient group than in the severe SIRS patient group: SAPS II 36±11 vs. SAPS II 47±14. But there were also patients in the non SIRS group with very high values of SAPS II (6 patients with SAPS II values superior to 35).

TABLE 2

Selenoprotein P plasma concentration at admission in ICU patients

| Groups | Septic shock or severe SIRS patients | Non severe SIRS patients | Healthy volunteers |
| --- | --- | --- | --- |
| number of patients | (9 patients) (measurement at admission on only 8 patients) | (12 patients) | (7 volunteers) |
| Selenoprotein P | 17 ± 12 nmol/L (1-38) | 55 ± 45 nmol/L (20-181) | 49 ± 8 nmol/L (39-65) |

(p < 0.01 vs. healthy volunteers)
(p < 0.05 vs. non severe SIRS patients)
SIRS: Systemic Inflammatory Response Syndrome Initial dosages of the 7 patients admitted for septic shock were all inferior to 30 nmol/L. In this group, 4 patients required epinephrine or norepinephrine at doses superior to 0.1 µg/kg·min, corresponding to a cardiovascular scale value in the SOFA score of 4, which is the maximum cardiovascular dysfunction. In these 4 patients, 3 had a selenoprotein P value less than 15 nmol/L at their initial measurement. Three of these 4 patients died as a consequence of their septic shock. All of these three patients had had initially, at admission, a plasma selenoprotein P concentrations inferior to 15 nmol/L.

Moreover, selenoprotein P plasma concentration decreased further between admission and the first weekly measurement. Their values were inferior to 10 nmol/L in 3 out of the 7 patients in septic shock, and inferior to 16 nmol/L for 6 out of the 7 septic shock patients. The only septic shock patient who had a persistent selenoprotein P plasma concentration at 28 nmol/L at the first weekly measurement survived.

Example 3

Other SIRS Patients

In the severe SIRS group, one patient had at admission only a severe sepsis, retrospectively diagnosed as *Bordetella pertuissis*, associated with severe asthma. Her selenoprotein P plasma concentration at admission was the highest observed in the severe SIRS group: 38 nmol/L. A rapid decrease of the selenoprotein P plasma concentration to a concentration of 7.5 nmol/L was observed, simultaneously as she developed a very severe Adult Respiratory Distress Syndrome (ARDS), requiring 100% $FiO_2$ ventilation, with high level of positive end expiratory pressure, nitric oxide and prone-supine positions.

In the severe SIRS group, another patient was a severe polytrauma patient. This 34 year old man had severe thoracic and abdominal injuries requiring emergency surgery. In addition, his both femurs were broken and he had also a broken left humerus. He was initially in shock, and required abundant transfusion. He developed a severe rabdomyolisis, and a very convincing clinical and biological picture of severe fat embolism, and later, infection was suspected. Iri this patient, the selenoprotein P plasma concentration was low at admission (selenoprotein P: 10 nmol/L) and remained low during his ICU length of stay. He was discharged from ICU to the orthopedic ward in less than three weeks.

As selenoprotein P is stable in the general population and as this young polytrauma patient was healthy before his accident, such a low initial plasma selenoprotein P concentration indicates that the marked decrease of selenoprotein P observed in the severe SIRS group rapidly appears in the case of a severe SIRS.

Example 4

Non Severe SIRS Patients

In the non severe SIRS group, four patients out of 12 had a selenoprotein P plasma concentration between 20 and 30 nmol/L at there initial measurement. One of them belongs to a selenium deficient group (chronic dialysis); and two were misclassified as they had ischemia-reperfusion injuries (one with a status epilepticus well known to have transient lactate acidosis, and the other an inferior leg vascular cross clamping followed by hemorrhage and myocardial infarcts).

On the opposite, high level of selenoprotein P was observed in the non severe ICU SIRS patients; in this group, 6 patients had a selenoprotein P plasma concentration superior to 60 nmol/L, even in ICU patients with high SAPS II value.

Indeed, there is little correlation between SAPS II gravity index score, and the selenoprotein P plasma concentration for the all patients (r=0.33). There was also little correlation between SAPS II gravity index score, and the selenoprotein P plasma concentration in the severe SIRS patient group (r=0.25). One should underlined that fact, as SAPS II gravity index score reflects the probability of death of ICU patients, but not the specific gravity of the SIRS or septic shock (From Celsus to Galen to Bone: The Illnesses, Syndromes, and Diseases of Acute Inflammation, Marshall J C, Aarts M A, in Yearbook of Intensive Care and Emergency Medicine, Vincent JL ed.; Springer Verlag, 2001; 3-12). Mean SAPS II gravity index score was lower in the non severe SIRS patients, 47±14 vs. 36±11 (p=0.055) than in the severe SIRS patients. However, the mortality rate of the two group was close with 3 deceased patients out of 9 in the severe SIRS patient group (all of them septic shock patients) and 3 deceased patients out of 12 in the non severe SIRS patient group.

Example 5

Gravity Index, Follow-Up

One should underlined that the last selenoprotein P plasma concentration observed before death were significantly lower (p<0.05) in the 3 deceased septic shock patients, compared to the 3 deceased patients of the non SIRS group (see Table 3 below).

Moreover, the surviving patient with a very low selenoprotein P plasma concentration of 3 nmol/L at his last dosage before discharge from ICU was an anorexic patient, with therefore an initial selenium deficiency, which had made during his ICU length of stay several severe nosocomial infections, including 2 nosocomial peritonitis, following the initial peritonitis. This patient had at his discharge a persistent abundant enteric fistula.

The mean selenoprotein P plasma concentration of the surviving severe SIRS patients observed before discharge was 23 nmol/L compared to 10 nmol/L for the deceased severe SIRS patients. However, it is to be noticed that selenium supplementation was only 40 µg per day, according to the daily recommended intake. This supplementation is probably very insufficient, in such inflammatory patients. (Selenium and the "free" electron"—Selenium a trace to be followed in septic or inflammatory ICU patients, Forceville X, Intensive Care Medicine; 2001, 27: 16-18). Indeed, as for all selenoprotein, the syntheses of selenoprotein P requires available selenium.

Selenoprotein P is a good marker for the follow-up of selenium supplementation or treatment in inflammatory ICU patients.

TABLE 3

| Groups | Selenoprotein P plasma concentration at the latest value before ICU discharge | | |
|---|---|---|---|
| | Septic shock or severe SIRS patients | Non severe SIRS patients | |
| deceased patients | (3 patients) (all septic shock patients) | (3 patients) (non SIRS diseased patients) | |
| Selenoprotein P | 10 nmol/L (0-24) | 49 (27-84) | P < 0.05 |
| ICU surviving patients | (6 patients) | (9 patients) | |
| Selenoprotein P | 23 nmol/L (3-60) | 41(20-77) | |

Results are given in mean ± standard deviation; followed by minima and maxima in barkets
SIRS: Systemic Inflammatory Response Syndrome.

What is claimed is:

1. A method for diagnosing severe Systemic Inflammation Response Syndrome (severe SIRS) or septic shock involving an inflammatory reaction within a patient, wherein said method comprises the steps of:
   (a) providing a blood sample from said patient;
   (b) providing a plurality of control samples wherein each control sample contains a predetermined concentration of selenoprotein P as a control reference;
   (c) determining the concentration of selenoprotein P which is contained in the blood sample by measuring the amount of the selenoprotein P in the blood sample, and measuring the amount of the selenoprotein P in the control samples, and then comparing the measured amount in the blood sample to the measured amount in the control samples to determine the concentration of selenoprotein P in the blood sample, wherein the determination of the selenoprotein concentration is performed by an immunoassay using antibodies directed against selenoprotein P; and
   (d) diagnosing that said patient does not have severe SIRS or septic shock when the selenoprotein P plasma concentration which is determined at step (c) is equal to or higher than 40 nmol/L, and diagnosing that said patient has severe SIRS or septic shock when the selenoprotein P plasma concentration which is determined at step (c) is equal to or lower than 30 nmol/L.

2. The method according to claim 1, wherein the blood sample consists of a blood plasma sample.

3. A method for monitoring severe Systemic Inflammation Response Syndrome (severe SIRS) or septic shock involving an inflammatory reaction within a patient, wherein said method comprises the steps of:
   (a) taking a blood sample from said patient, respectively i) prior to said patient being monitored and ii) during the time period wherein said patient is being monitored;
   (b) providing a plurality of control samples wherein each control sample contains a predetermined concentration of selenoprotein P as a control reference;
   (c) determining the concentration of selenoprotein P which is contained in the blood samples obtained at step a) by measuring the amount of selenoprotein P which is contained in the blood samples obtained at step a), and measuring the amount of the selenoprotein P in the control samples, and then comparing the measured amount in the blood samples to the measured amount in the control samples to determine the concentration of selenoprotein P in the blood samples, wherein the determination of the selenoprotein P concentration is performed by an immunoassay using antibodies directed against selenoprotein P; and
   (d) comparing the concentration of selenoprotein P determined at step (c) for the samples taken i) prior to said patient being monitored and ii) during the time period wherein said patient is being monitored; and
   (e) measuring an increase or a decrease of said selenoprotein P concentration in step (d), whereby said increase or decrease assists in monitoring severe SIRS or septic shock involving an inflammatory reaction.

4. The method according to claim 3, wherein the blood sample consists of a blood plasma sample.

5. The method according to claim claim 1, further comprising diagnosing severe SIRS or septic shock when the amount of selenoprotein P plasma concentration measured at step (c) is less than 20 nmol/L.

* * * * *